United States Patent
Theobald et al.

(10) Patent No.: US 7,162,069 B2
(45) Date of Patent: Jan. 9, 2007

(54) OBJECTIFICATION OF SURFACE TEST METHODS THROUGH IMAGE PROCESSING

(75) Inventors: Stefan Theobald, Senden (DE); Manfred Heinrich, Bellenberg (DE); Petra Ritter, Voehringen (DE)

(73) Assignee: Wieland-Werke AG, Ulm (DE)

(*) Notice: Subject to any disclaimer, the term of this patent is extended or adjusted under 35 U.S.C. 154(b) by 661 days.

(21) Appl. No.: 10/400,314

(22) Filed: Mar. 27, 2003

(65) Prior Publication Data

US 2003/0185430 A1 Oct. 2, 2003

(30) Foreign Application Priority Data

Mar. 28, 2002 (DE) .............. 102 13 910

(51) Int. Cl.
*G06K 9/00* (2006.01)
(52) U.S. Cl. .............. 382/141; 73/105; 356/600
(58) Field of Classification Search .............. 356/512, 356/521, 604, 600; 382/141; 703/168, 189; 73/104, 105

See application file for complete search history.

(56) References Cited

U.S. PATENT DOCUMENTS

| | | | | |
|---|---|---|---|---|
| 5,307,151 A | * | 4/1994 | Hof et al. ............... | 356/604 |
| 5,311,286 A | | 5/1994 | Pike | |
| 5,379,107 A | | 1/1995 | Hanssen et al. | |
| 5,403,373 A | * | 4/1995 | Kitagawa et al. ........ | 75/238 |
| 5,568,256 A | * | 10/1996 | Korner et al. ........... | 356/512 |
| 6,122,065 A | | 9/2000 | Gauthier | |
| 6,197,387 B1 | * | 3/2001 | Fiedler et al. .......... | 427/532 |
| 6,731,886 B1 | * | 5/2004 | Takeda .................. | 399/45 |
| 6,776,030 B1 | * | 8/2004 | Kirpichnikov et al. ... | 73/105 |
| 2003/0185430 A1 | * | 10/2003 | Theobald et al. ........ | 382/141 |

FOREIGN PATENT DOCUMENTS

| | | |
|---|---|---|
| DE | 42 17 768 | 12/1993 |
| DE | 43 15 202 | 11/1994 |
| DE | 196 35 072 | 3/1998 |
| EP | 0 893 669 | 1/1999 |

OTHER PUBLICATIONS

Wieland-Kupferwerkstoffe—6$^{th}$ Edition 1999, pp. 233-235.
ASTM Designation: B 820-98, entitled: Standard Test Method for Bend Test for Formability of Copper Alloy Spring Material, 1998, pp. 802-804.
Deutsche Norm, Metallische Werkstoffe Biegeversuch—DIN EN ISO 7438, Jul. 2000, (8 pages).

* cited by examiner

*Primary Examiner*—Gregory Desire
(74) *Attorney, Agent, or Firm*—Flynn, Thiel, Boutell & Tanis, P.C.

(57) ABSTRACT

The invention relates to the objectification of surface test methods through image processing. Information z(x, y) is measured and recorded for each image point (x, y) of the measuring field of an examined specimen surface, and resultant magnitudes are calculated therefrom. An objective correlation of these resultant magnitudes occurs with a scale of so far subjectively measured quality characteristic numbers of a characteristic of the examined specimen. A method for an objective evaluation of a bending edge of metal bands and for a wear test on metal bands is described in detail.

6 Claims, 5 Drawing Sheets

CLASSIFICATION OF BENT CORNERS

```
Order Data:                            Test Data:
    Order Number:          00000           Date:                        24 JAN 2002
    Specimen Number:       00000           Time:                        14:13:28
    Specimen Identification: 1P0.6F        Tester:                      MFP/Th
    Alloy:                 B18             Rolling Orientation:         0°
    Coating:               none            Bend Angle:                  90°
    Specimen Thickness s [mm]: 0.3         Bend Radius r [mm]:          0.6
    Specimen width b [mm]: 10.00           Measuring-Field Width [mm]:  0.42
                                           Measuring-Field Length [mm]: 3.40

Remarks:

Evaluation:
    Strategy:              Standard        Measuring-Field Width Changed:  NO
    Roughness Parallel:    0.37 µm         Measuring-Field Length Changed: NO
    Roughness Vertical:    0.82 µm         Ratio r/s:                      2.00
    Surface Class:                         Ratio b/s:                      33.33
    (Calculated)           2.8             Evaluation (Visual):            3
```

LIVE IMAGE              HEIGHT IMAGE

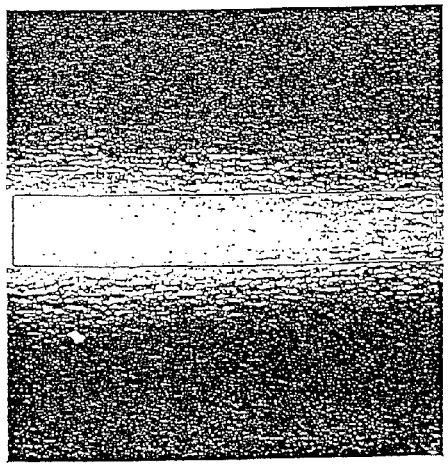 

Fig. 5

OBJECTIFICATION OF SURFACE TEST METHODS THROUGH IMAGE PROCESSING

FIELD OF THE INVENTION

The invention relates to the application of a method for the image processing for the objective evaluation of characteristics of an examined specimen surface.

BACKGROUND OF THE INVENTION

When examining the surface of metal bands, in particular metal bands consisting of Cu or Cu-alloys, it is often the case that indeed directives exist for the manufacture of the specimens to be examined, however, the result of the test is determined through a subjective comparison by the observer with a preset standard series so that the result of the test depends among others on the skill and the experience of the tester.

This is, for example, the case when evaluating the bending edge of metal bands.

Specimens for the bend test are manufactured corresponding to EN 7438:2000 using suitable bending punches and matrixes. The bend specimens are characterized by thickness s, width b, bend radius r, bend angle and bend direction relative to the rolling direction (see FIGS. 1 and 2) [compare Wieland-Handbuch "Kupferwerkstoffe" ($6^{th}$ Edition 1999, Pages 233–235), there: WR=rolling direction, BK=bending edge]. Usually specimens with a 90° or 180° bend angle are utilized. The specimen widths vary between 0.25 mm and 20 mm, the thickness extends from 0.10 mm to 2 mm, the bend radii assume values between 0 mm and 10 mm.

The ASTM Designation B 820-98 discloses directives for carrying out the testing. The bend samples are at present examined under the stereomicroscope (enlargement usually 10 times). A division into six classes takes place:

| Class | Evaluation Text |
|---|---|
| 1 | smooth, no cracks |
| 2 | slightly rough, slight orange peel, no cracks |
| 3 | orange peel to strong orange peel, no cracks |
| 4 | starting to crack, incipient cracks |
| 5 | cracks to strong cracks |
| 6 | specimen broken |

The occurrence of incipient cracks in the bending edge counts as error criterion.

The results are documented by indicating the bend radius at which a crack does not quite yet occur, together with the bend angle and bend direction. Since this method is not quantitative, the exactness of this test method with regard to the bending ability of the examined material cannot be indicated. The result of the method depends furthermore on the tester.

SUMMARY OF THE INVENTION

Starting out from this special case, the basic purpose of the invention is therefore to provide a quantitative method, independent of the tester carrying out the test, for evaluating the specimen surface, which method in addition also operates essentially automatically and logs and documents the results.

The purpose is attained according to the invention by a method of image processing.

According to a particular embodiment of the invention, a method of strip projection, which determines the three-dimensional surface topography, is applied to the test surface for an objective evaluation of the bending edge of metal bands.

Several known picture half-tone patterns (strips) are in the mentioned method pictured on an unknown surface topography and are photographed by a camera. The device calculates from the pictures of the strip images with known algorithms for each image point (x, y) the height information h(x, y). From this it is possible to calculate, analogous to the contact stylus method, optically detected surface roughness values. This method as such is indeed known (compare, for example, DE-OS 4 217 768), however, a transition to the evaluation of the bending edge has up to now not been done.

A further preferred embodiment of the invention is the application of the half-tone picture processing to an objective working of the wear test on metal bands.

BRIEF DESCRIPTION OF THE DRAWINGS

FIG. 5 is a sample classification report concerning a tested specimen;

DETAILED DESCRIPTION

Figure 6:
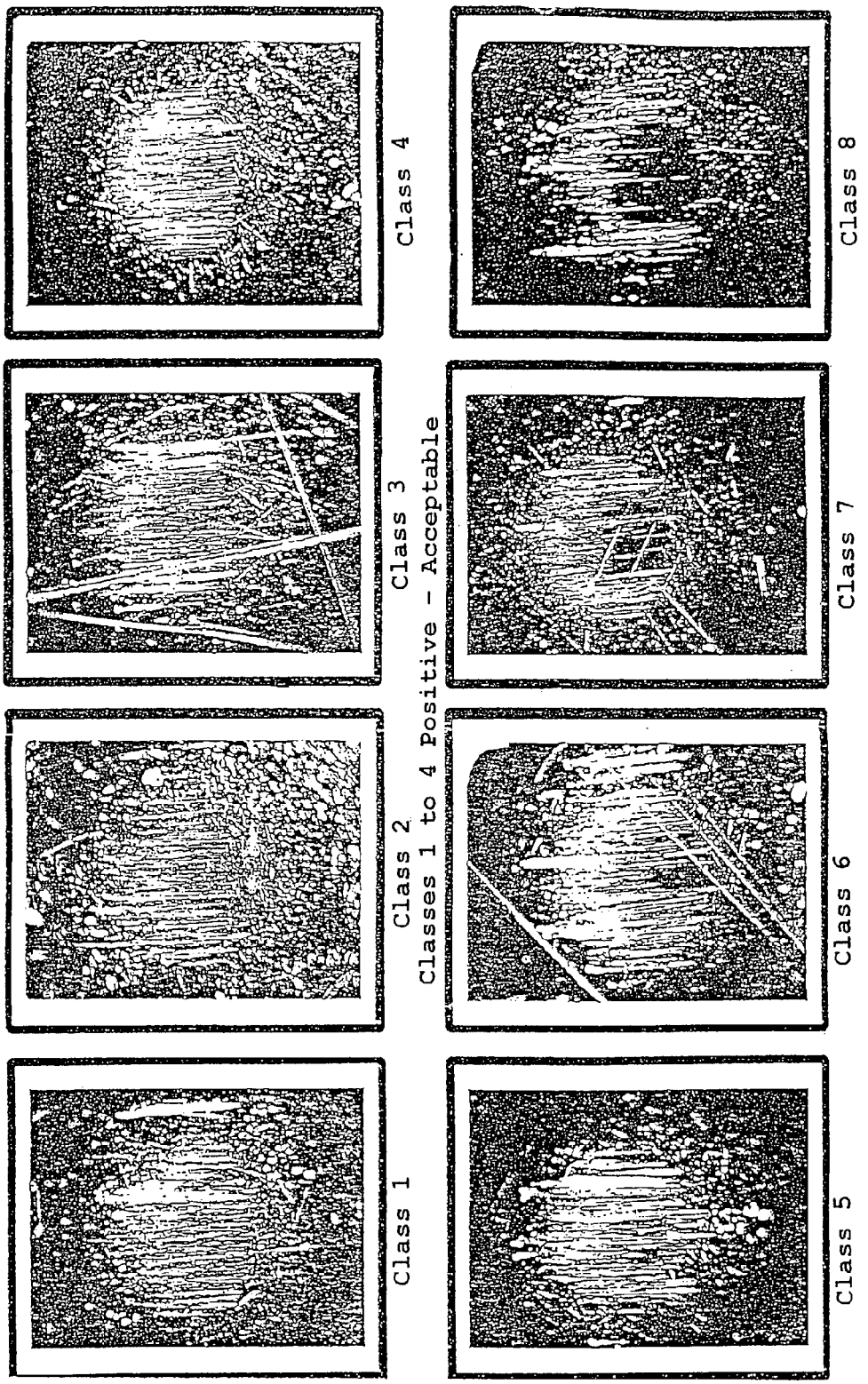
FIG. 6 is a sampling of specimen classification data resulting from the wear test.
Figure 7:
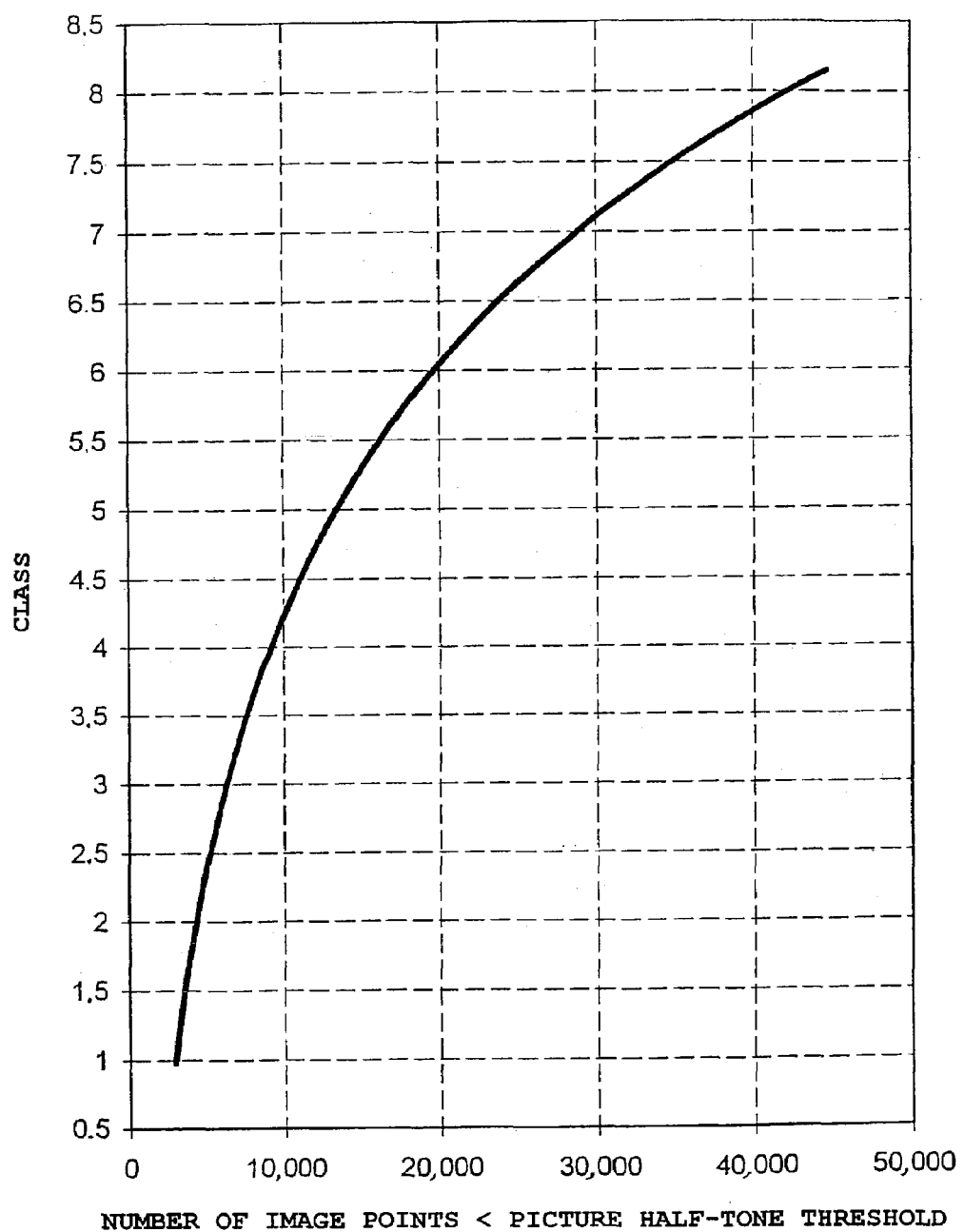
FIG. 7 is a graph depicting specimen classification in accordance with gray scale data.

The invention is discussed in connection with FIGS. 3 to 5 for the bending edge testing, and in connection with FIGS. 6 and 7 for the wear test.

Figure 1:
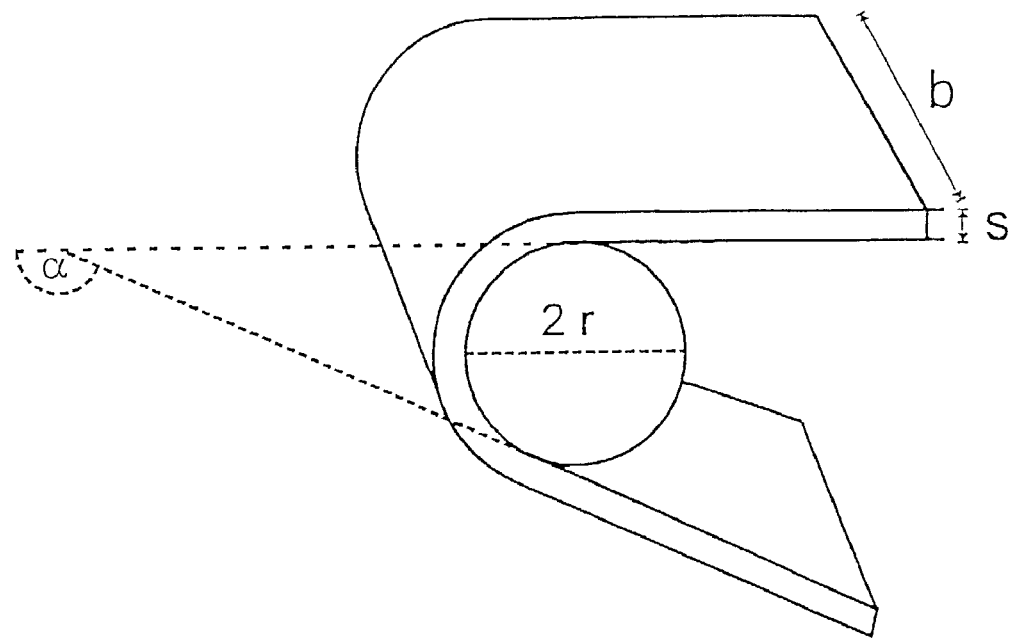
FIG. 1 is a schematic view of a bent specimen.
Figure 2:
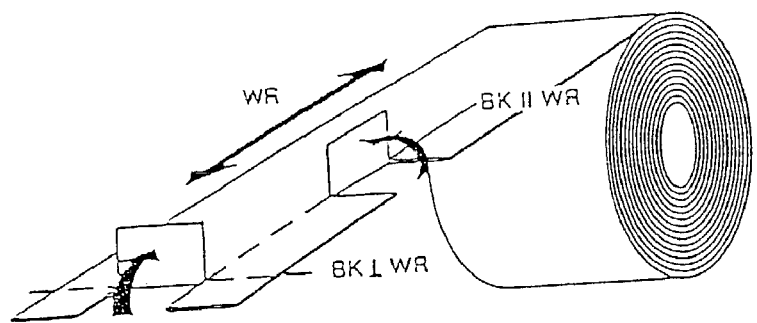
FIG. 2 is a further schematic view of a bent specimen and depicting several bends in relation to the rolling direction.
Figure 3:
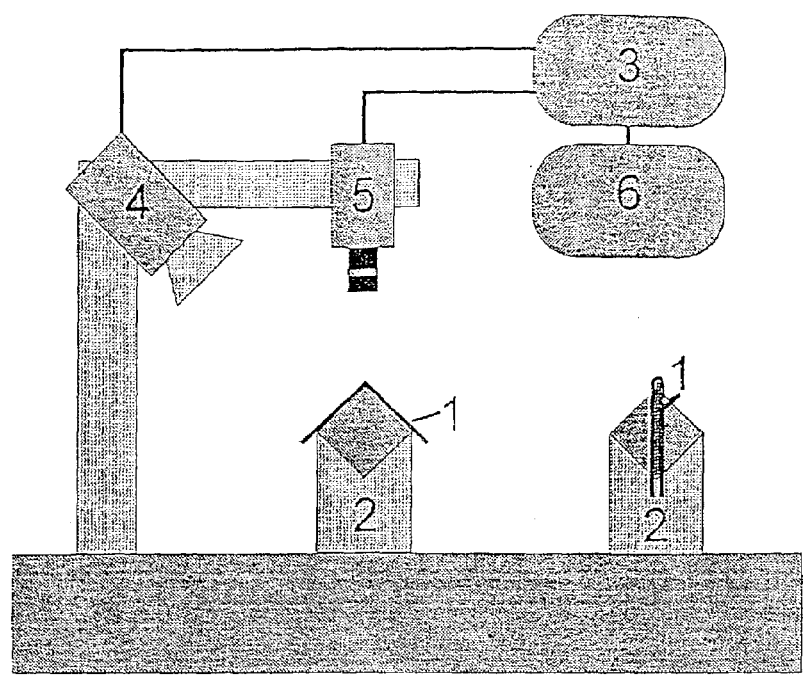
FIG. 3 is a view of a specimen testing arrangement embodying the invention.
Figure 4:
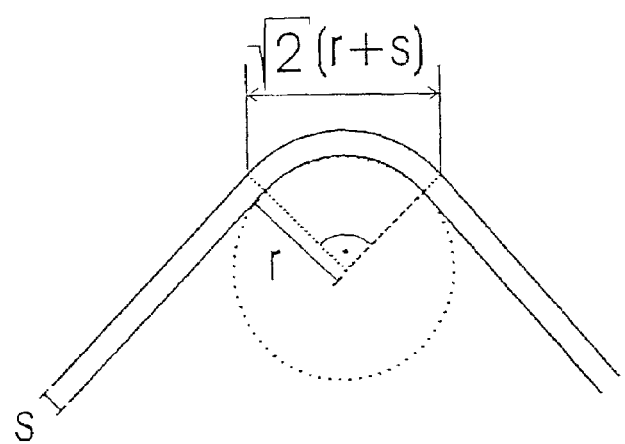
FIG. 4 is a still further schematic view of a bent specimen.

1) The measuring system for testing of the bending edge is schematically illustrated in FIG. 3.

The specimen 1 is fixed on a suitable mounting 2 (90° bent specimen on rhombus, 180° bent specimen, open leg on edge, 180° bent specimen, closed leg clamped). The specimen surface is illustrated as a camera picture on a monitor in the control and evaluating computer 3. The operator carries out a focus adjustment by changing the distance between specimen 1 and projector 4/camera unit 5. The measuring field length corresponds according to standard to the width of the maximum viewable measuring field (in this case 3.40 mm), however, it can be adjusted optionally smaller. The measuring field width is calculated from the bend radius r and specimen thickness s (FIG. 4) and is preadjusted to $\sqrt{2}/3$ (r+s), and can be enlarged to a maximum viewable measuring field width of 2.5 mm. The lateral resolution is 4.4 µm per image point. A sequence of strip patterns is projected onto the bend specimen 1 with a projector 4, and is photographed by a camera 5. The light of the strip patterns is reflected either diffuse or directly in a certain angle into the objective of the matrix-camera (usually of CCD-type). The strip pattern is generated with a halogen light and a micro mirror device. A plane surface will result in straight strip lines recorded by the camera. A structured surface (height differences) causes an elongation or curvature of the projected strips. Consequently, the three dimensional topography of the sample surface can be measured by evaluating the two dimensional pictures of the strip patterns. In the special case, the strips are projected perpendicular to the bending edge. Projector 4 and camera 5 are controlled by a computer 3 through suitable interface cards. The operation occurs also through the graphic operating surface of the computer 3. The measuring occurs completely automatically. The saddle-shaped specimen form created during bending is mathematically described by a polynomial surface. The polynomial surface is then subtracted from the measured data (calculated leveling of the bending edge). Deviations of the measured data from this surface are then due to roughnesses, incipient cracks or cracks. Medium roughness values parallel $R_x$ and vertical $R_y$ to the bending edge, surface roughness and maximum roughness depth $R_{max}$ are determined from the data. The measured height data is given in matrix type h(x, y). x labels the index of the n columns, y the index of the m rows. There are n columns and m rows. n,m are given by the relation of the dimensions of the measuring to the lateral resolution (here 4.4 μm) of the device. $R_{max}$ is given by the difference of the maximal h(x, y) and the minimal h(x, y).

For the calculation of $R_x$ and $R_y$ the following steps are performed:

i) calculation of average $\bar{h}$ for each row and column.

$$\text{column:} \quad \bar{h}(x) = \frac{1}{m} \sum_{y=1}^{m} h(x, y);$$

$$\text{row:} \quad \bar{h}(y) = \frac{1}{n} \sum_{x=1}^{n} h(x, y);$$

ii) calculation of the absolute deviation of each point (x,y) to the average of column respective row:

column: $\Delta x(x,y) = |h(x,y) - \bar{h}(x)|$ row: $\Delta y(x,y) = |h(x,y) - \bar{h}(y)|$ iii) calculation of the average, absolute deviation of each column $$x: \quad \overline{\Delta x}(x) = \frac{1}{m} \sum_{y=1}^{m} \Delta x(x, y)$$

of each row $$y: \quad \overline{\Delta y}(y) = \frac{1}{n} \sum_{x=1}^{n} \Delta y(x, y)$$

iv) and as a result, the average roughness along the bending edge $R_x$ and across the bending edge $R_y$:

$$R_x = \frac{1}{m} \sum_{y=1}^{m} \overline{\Delta y}(y);$$

$$R_y = \frac{1}{n} \sum_{x=1}^{n} \overline{\Delta x}(x).$$

A resultant magnitude is calculated from the magnitudes (here: resultant magnitude=0.5*($R_x$+$R_y$)). The surface class is calculated from the resultant magnitude through a clear, functional interrelationship. The surface class is calculated from the resultant magnitude by an equation of the form $$\text{surface class} = A \cdot \log\left(\frac{\text{resultant magnitude}}{B}\right),$$

where the parameters A and B can depend on the examined material (alloy, surface layers, ... ). The test parameters and test results are illustrated on the image screen of the control computer 3 and are recorded in a suitable manner (for example FIG. 5). The data is automatically stored in data files 6.

2) The wear test is a testing method for the qualitative evaluation of the punching quality (tool life) of sheet metal and bands. The up to now visual evaluation of the spherical surface carried out by the operator is objectified by the hereinafter described method.

According to the present state of the art, a test ball eccentrically clamped in a holder is pressed with a constant force onto the specimen surface (in particular bands made of Cu or Cu-alloys). While the holder rotates with the ball (material: chromium steel), the specimen is pulled beneath the ball. Thus the ball slides spiral-like on the specimen surface. The contact surface of the ball with the band is subsequently viewed and evaluated in the stereomicroscope. The ball is polished when the band surface is hard. Polished, thus worn ball surfaces do not reflect any light in the dark field into the microscope lens, thus appear black. The tester evaluates subjectively the portion of the surface appearing in black and then carries out a classification using a standard series in 8 classes (FIG. 6).

According to the invention, the portion of the worn ball surface is to be determined by measuring methods.

The microscope for viewing the ball surface is in addition supplemented with a CCD camera with a tubular barrel adapter for taking pictures. The image section of the CCD camera corresponds approximately to the section which the observer sees in the ocular of the microscope. The image detection occurs in an evaluating unit, which is equipped with suitable image-detecting hardware and image-processing software. The image is loaded through the camera into the store of the evaluating unit and is present there as a matrix of image points (x, y). Each image point carries as information a picture half-tone between 0 (=black) and 255 (=white). The number of the image points (pixels) is given by the CCD-matrix-camera and is, in this case, 730 columns and 580 rows.

The method determines based on the medium picture half-tone and the picture half-tone control of the not worn ball surface a threshold value. The threshold value is especially given by an equation of the form threshold value = average gray value of the surface before wear − standard deviation of the gray values of the surface before wear.

Picture half-tones smaller than this threshold originate from polished areas of the ball surface. By counting the image points with picture half-tones below the threshold, the surface portion of the polished surface can be calculated and a corresponding classification can be carried out (FIG. 7). The classification depends on the portion of the polished surface. The number of pixels with gray values smaller than the threshold value increases quadratically with the lateral dimensions of the polished surface portion.

A calibrating measurement of a not worn area of the ball surface is carried out prior to the test. After application of the wear stress, the surface is again viewed at the same area. The image viewed by the microscope is shown on the picture screen. The focused image is fixed by pushing a button. The tester selects the portion of the contact surface of the ball to be evaluated using the scrollable frame on the picture screen.

The evaluation is triggered by pushing a button on the control panel. The result is indicated as a grade number of 0.5 to 8.5 with a following decimal place.

What is claimed is:

1. A method for an objective evaluation of a flexible bending edge of metal bands made of Cu or Cu alloys, in which the three-dimensional topography of the bending edge is measured by strip-projection methods, and a height information $h(x,y)$ is thereby measured for each image point $(x,y)$ of a measuring field, and calculated as resultant magnitudes from the height information of average roughness values, wherein for calculating individual roughness values, a mathematically described specimen form is subtracted from the height information $h(x,y)$, wherein a classification of the bending edge is carried out with the resultant magnitudes.

2. The method according to claim 1, wherein a presetting of the measuring-field magnitude occurs according to the specimen geometry given by bend radius r and specimen thickness s.

3. The method according to claim 1, wherein the average roughness value is composed of roughness values lengthwise and roughness values transverse to the bending edge.

4. A method for objective evaluation of a flexible bending edge of a metal band by processing image data from an optical image-detecting unit with a digital evaluating unit including software algorithms, comprising the steps of:

measuring a three-dimensional topography of a surface of the bending edge, including measuring height information $h(x,y)$ for each image point $(x,y)$ of a measured field;

mathematically describing a specimen form created during bending as a polynomial surface;

calculating average roughness values $R_x$, $R_y$ along the bending edge and across the bending edge by using the height information $h(x,y)$;

calculating a resultant magnitude from the average roughness values $R_x$, $R_y$; and classifying the bending edge based on the resultant magnitude.

5. The method of claim 4, including the steps of:

calculating a measuring field width from a band radius r and specimen thickness s; and displaying test results on an image screen of a controller.

6. The method of claim 5, wherein the band is made of Cu or Cu-alloys and the method includes the step of storing the test results in data files.

* * * * *